US010408827B2

(12) United States Patent
Yamamoto et al.

(10) Patent No.: US 10,408,827 B2
(45) Date of Patent: *Sep. 10, 2019

(54) DETECTION OF BIOLOGICAL MOLECULES USING SURFACE PLASMON FIELD ENHANCED FLUORESCENCE SPECTROSCOPY (SPFS) COMBINED WITH ISOTACHOPHORESIS (ITP)

(71) Applicants: KONICA MINOLTA LABORATORY U.S.A., INC., San Mateo, CA (US); The Board of Trustees of the Leland Stanford Junior University, Stanford, CA (US)

(72) Inventors: Noriaki Yamamoto, Tokyo (JP); Juan Santiago, Stanford, CA (US); Denitsa Milanova, Boston, MA (US)

(73) Assignees: KONICA MINOLTA LABORATORY U.S.A., INC., San Mateo, CA (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,345

(22) Filed: Nov. 21, 2017

(65) Prior Publication Data
US 2018/0095080 A1   Apr. 5, 2018

Related U.S. Application Data

(63) Continuation of application No. 15/071,714, filed on Mar. 16, 2016, now Pat. No. 9,939,435, which is a continuation-in-part of application No. 14/995,112, filed on Jan. 13, 2016, now abandoned.

(60) Provisional application No. 62/102,673, filed on Jan. 13, 2015.

(51) Int. Cl.
G01N 33/543    (2006.01)
B01L 3/00      (2006.01)
G01N 27/447    (2006.01)
G01N 21/64     (2006.01)

(52) U.S. Cl.
CPC .... *G01N 33/54373* (2013.01); *B01L 3/50273* (2013.01); *B01L 3/502715* (2013.01); *B01L 3/502761* (2013.01); *G01N 21/648* (2013.01); *G01N 27/44791* (2013.01); *B01L 2200/027* (2013.01); *B01L 2300/0627* (2013.01); *B01L 2300/0654* (2013.01); *B01L 2300/0867* (2013.01); *B01L 2300/0877* (2013.01); *B01L 2300/12* (2013.01); *B01L 2300/16* (2013.01); *B01L 2400/0421* (2013.01); *G01N 2021/6482* (2013.01)

(58) Field of Classification Search
CPC ............ G01N 33/54373; G01N 21/648; B01L 3/502715
See application file for complete search history.

(56) References Cited

U.S. PATENT DOCUMENTS

| 2009/0213383 A1 | 8/2009 | Ly et al. |
| 2013/0078148 A1 | 3/2013 | Kaya et al. |
| 2013/0175173 A1 | 7/2013 | Ivory et al. |
| 2015/0197791 A1 | 7/2015 | Yamamoto |

FOREIGN PATENT DOCUMENTS

WO        2011155435 A1    12/2011

OTHER PUBLICATIONS

Bercovici et al., "Rapid Detection of Urinary Tract Infections Using Isotachophoresis and Molecular Beacons," Analytical Chemistry, 2011, 83, pp. 4110-4117.
Han et al., "Increasing hybridization rate and sensitivity of DNA microarrays using isotachophoresis", Lab Chip, 2014, 14, pp. 2958-2967.
Liebermann et al., "Surface-plasmon field-enhanced fluorescence spectroscopy", Colloids and Surfaces A: Physicochemical and Engineering Aspects, 171, 2000, pp. 115-130.
Knoll et al., "Principles and Applications of Surface-Plasmon Field-Enhanced Fluorescence Techniques", Topics in Fluorescence Spectroscopy, vol. 8: Radiative Decay Engineering, Edited by Geddes and Lakowicz, Springer Science+Business Media, Inc., New York, 2005, pp. 305-332.
Gerasimova et al., "RNA-Cleaving Deoxyribozyme Sensor for Nucleic Acid Analysis: The Limit of Detection", Chembiochem, 2010, 11, pp. 811-817.
Bercovici et al., "Rapid hybridization of nucleic acids using isotachophoresis," Proc Natl Acad Sci, 2012, vol. 109, No. 28, pp. 11127-11132.
Garcia-Schwarz et al., "Integration of on-chip isotachophoresis and functionalized hydrogels for enhanced-sensitivity nucleic acid detection," Analytical Chemistry, 2012, 84, pp. 6366-6369.

(Continued)

*Primary Examiner* — Narayan K Bhat
(74) *Attorney, Agent, or Firm* — Chen Yoshimura LLP

(57) ABSTRACT

A combination of surface plasmon field enhanced fluorescence spectroscopy (SPFS) and isotachophoresis (ITP) technologies for detecting biomolecules is disclosed. It uses ITP to preconcentrate the reactants and accelerate the reaction, and then delivers the reacted sample to an SPFS sensor for detection. A microfluidic device with a T-junction is provided, which has two reservoirs respectively containing a low-mobility trailing electrolyte buffer and a high-mobility leading electrolyte buffer, and a main fluid channel between the two reservoirs, where the SPFS sensor is located on a side channel joined to the main channel. A two-step technique is employed, including a step of sample loading and ITP extraction, and a step of delivery of concentrated sample to the detector chamber by pressure-driven flow. In another embodiment, the SPFS sensor is located on the main fluid channel between the two reservoirs. In a particular example, the technique is used in a DNAzyme assay.

12 Claims, 13 Drawing Sheets

(56) References Cited

OTHER PUBLICATIONS

George, "Atomic Layer Deposition: An Overview", Chemical Reviews, 2010, vol. 110, No. 1, pp. 111-131.
Lin et al., "Leakage current and breakdown electric-field studies on ultrathin atomic-layer-deposited $Al_2O_3$ on GaAs", Applied Physics Letters, 2005, 87, 182904.
Usui et al., "Approaching the limits of dielectric breakdown for $SiO_2$ films deposited by plasma-enhanced atomic layer deposition", Acta Mater, 2013, http://dx.doi.org/10.1016/j.actamat.2013.09.003.
Liebermann et al., "Complement hybridization from solution to surface-attached probe-oligonucleotides observed by surface-plasmon-field-enhanced fluorescence spectroscopy", Colloids and Surfaces A: Physicochemical and Engineering Aspects, vol. 169, Sep. 2000, pp. 337-350.

DETECTION OF BIOLOGICAL MOLECULES USING SURFACE PLASMON FIELD ENHANCED FLUORESCENCE SPECTROSCOPY (SPFS) COMBINED WITH ISOTACHOPHORESIS (ITP)

BACKGROUND OF THE INVENTION

Field of the Invention

This invention relates to a method that uses surface plasmon field enhanced fluorescence spectroscopy (SPFS) and isotachophoresis (ITP) to achieve ultra-rapid and highly-sensitive biological molecules detection.

Description of Related Art

Surface plasmon field-enhanced fluorescence spectroscopy (SPFS) is a known biosensing technology. See T. Liebermann, W. Knoll, Surface-plasmon field-enhanced fluorescence spectroscopy, Colloids and Surfaces A: Physicochem. Eng. Aspects 171 (2000) 115-130 ("Liebermann 2000"); Wolfgang Knoir, Fang Yu, Thomas Neumann, Lifang Niu, and Evelyne L. Schmid, Principles And Applications Of Surface Plasmon Field-Enhanced Fluorescence Techniques, in Topics in Fluorescence Spectroscopy, Volume 8: Radiative Decay Engineering, Edited by Geddes and Lakowicz, Springer Science+Business Media, Inc., New York, 2005, p. 305-332. These references are incorporated by reference in their entireties to show the principle and setup of SPFS biosensors in general. SPFS offers high-sensitivity detection through advanced sensing technology.

FIG. 1A of this application, taken from FIG. 5 of the Liebermann 2000 paper, illustrates the setup of an SPFS system. FIG. 1B of this application, taken from FIG. 6(a) of the same paper, illustrates the structure of the prism and flow cell used in the SPFS system. The basic concept of SPFS is described below with reference to FIGS. 1, 1A and 1B. An SPFS biosensor includes a thin metal film on a glass or plastic prism. The metal may be, for example, gold, silver, aluminum, etc. A capture molecule is immobilized on the surface of the metal film. A biological sample is applied on the metal film. When an incident light of a certain wavelength is irradiated on the prism at a certain angle, a strong electrical field is generated at the surface of the metal film. Because of quenching from the metal film, the best place for fluorescence excitation is in the region about a couple of tens to hundreds nm above the surface. In a typical device, the quenching region is within about 0-5 nm from the metal surface, and the enhanced region is about 10-200 nm from the surface. If a fluorescent label is trapped in this enhanced region, strong fluorescent signal is generated.

SPFS biosensors are based on fluorescence detection. In conventional SPFS biosensors, in addition to first antibodies that are immobilized on the thin metal film, fluorescent labeled second antibodies are generally used for protein detection. This is schematically illustrated in FIG. 1. The first antibodies 101 are immobilized on the thin metal film. The target 102 (i.e. substance to be detected, such as a protein) is added to the biosensor and captured on the immobilized first antibodies. Then, the fluorescent labeled second antibodies 103 are added to the biosensor and they bind to the target. The first antibody 101, the target 102 and the second antibody 103 form a structure such that the fluorescent label 103F on the second antibody is located in the region of enhanced electric field above the thin metal film, and a strong fluorescent signal is generated. For unbound second antibodies or those that form non-specific binding, their fluorescent labels tend to be located outside of the enhanced region, either in the metal quenching region or farther away from the surface, so they are not excited. The biosensor can be washed before the detection result is obtained. These multiple steps make the biosensor more complicated to use and the turnaround time long.

PCT application WO 2011155435 A1, Near field-enhanced fluorescence sensor chip, also describes surface plasmon field enhanced fluorescence spectroscopy.

Isotachophoresis (ITP) is an electrophoresis technique that uses two buffers including a high-mobility leading electrolyte (LE) and a low-mobility trailing electrolyte (TE). In peak-mode ITP, sample species bracketed by the LE and TE focus into a narrow TE-to-LE interface by application of an electric field of typically a few hundred volts per cm. Due to the high concentration of sample species in a small volume at the interface, high efficiency (rapid) molecular-molecular interaction can occur. ITP has been used, for example, to selectively extract and concentrate medically relevant biomarkers from body fluids such as whole blood and urine sample.

An ultra-rapid nucleic acid detection technology using ITP is described in Rapid Detection of Urinary Tract Infections Using Isotachophoresis and Molecular Beacons, M. Bercovici et al., Analytical Chemistry 2011, 83, 4110-4117 ("Bercovici et al. Analytical Chemistry 2011"). This method accelerates DNA hybridization by using ITP. FIG. 1 of this article, reproduced as FIG. 2 of the instant disclosure, shows the principle of detection. The article describes: "FIG. 1a schematically presents the principles of the assay. ITP uses a discontinuous buffer system consisting of LE and TE, which are typically chosen to have respectively higher and lower electrophoretic mobility than the analytes of interest. Both sample and molecular beacons are initially mixed with the TE. When an electric field is applied, all species with mobility higher than that of the TE electromigrate into the channel. Other species (including ones with lower mobility, neutral or positively charged) remain in or near the sample reservoir. Focusing occurs within an electric field gradient at interface between the LE and TE, as sample ions cannot overspeed the LE zone but overspeed TE ions." (Id., p. 4111, left column.) "FIG. 1. (a) Schematic showing simultaneous isotachophoretic extraction, focusing, hybridization (with molecular beacons), and detection of 16S rRNA bound to a molecular beacon. Hybridization of the molecular beacon to 16S rRNA causes a spatial separation of its fluorophore and quencher pair resulting in a strong and sequence-specific increase in fluorescent signal. (b) Raw experimental image showing fluorescence intensity of molecular beacons hybridized to synthetic oligonucleotides using ITP. (c) Detection of oligonucleotides having the same sequence as the target segment of 16S rRNA. Each curve presents the fluorescence intensity in time, as recorded by a point detector at a fixed location in the channel (curves are shifted in time for convenient visualization). 100 pM of molecular beacons and varying concentrations of targets were mixed in the trailing electrolyte reservoir. The total migration (and hybridization) time from the on-chip reservoir to the detector was less than a minute." (Id., p. 4111, right column.) A setup for the on-chip ITP assay using a microfluidic chip is shown in FIGS. 2A and 2B of the instant disclosure, reproduced from FIGS. 2 and 3(a) of the above article.

Han, C. M., Katilius, E., Santiago, J. G., "Increasing hybridization rate and sensitivity of DNA microarrays using isotachophoresis," Lab on a Chip 2014 discloses a method to increase hybridization between immobilized DNA probe and free DNA by ITP.

DNAzymes are DNA molecules that have the ability to catalyze specific chemical reactions. As nucleic acids, DNAzymes offer several advantages to enzymes, including increased thermal stability and pH resistance. They have been shown to be very specific, capable of differentiating between targets differing by as little as a single nucleotide. One application of DNAzymes is in the fluorescent detection of nucleic acid targets. Y. V. Gerasimova, E. Cornett, and D. M. Kolpashchikov, "RNA-Cleaving Deoxyribozyme Sensor for Nucleic Acid Analysis: The Limit of Detection", Chembiochem (2010), 11, 811-817 describes an assay in which a two-stranded DNAzyme is used to catalyze a reaction between a substrate internally labeled with both a fluorophore and quencher, and a 20-nucleotide DNA target. Both the substrate and the target are complementary to different sections of the DNAzyme. When the two strands of the DNAzymes, the substrate, and the target come together into one large complex, the DNAzyme cleaves the substrate, separating the fluorophore from the quencher and resulting in a signal increase. Once cleaved, the DNAzyme and target are free to react with another substrate, leading to signal amplification. This article demonstrated a 0.1 nM limit of detection, but the assay time was over 3 h.

SUMMARY

An object of this invention is to achieve ultra-rapid and highly-sensitive detection of biomolecules by combining ITP and SPFS technologies.

To achieve these and/or other objects, as embodied and broadly described, the present invention provides a microfluidic chip for detecting a biological analyte, which includes: a main fluid channel; a first reservoir containing a low-mobility trailing electrolyte (TE) buffer and connected to the main fluid channel at a first location; a second reservoir containing a high-mobility leading electrolyte (LE) buffer and connected to the main fluid channel at a second location; and a side fluid channel connected at its first end to the main fluid channel at a third location between the first reservoir and the second reservoir; and a detector chamber connected to a second end of the side channel, the detector chamber being equipped with a SPFS (surface plasmon field enhanced fluorescence spectroscopy) sensor, wherein the SPFS sensor has a metal surface which has capture molecules immobilized on it and which forms a part of an inner surface of the detector chamber.

In another aspect, the present invention provides a method for detecting a target analyte, which includes: providing a microfluidic chip which includes a main fluid channel, a first reservoir containing a low-mobility trailing electrolyte (TE) buffer and connected to the main fluid channel at a first location, a second reservoir containing a high-mobility leading electrolyte (LE) buffer and connected to the main fluid channel at a second location, a side fluid channel connected at its first end to the main fluid channel at a third location between the first reservoir and the second reservoir, and a detector chamber connected to a second end of the side channel, the detector chamber being equipped with a SPFS (surface plasmon field enhanced fluorescence spectroscopy) sensor, wherein the SPFS sensor has a metal surface which has capture molecules immobilized on it and which forms a part of an inner surface of the detector chamber; loading a sample mixture into the first reservoir of the microfluidic chip, wherein the sample mixture contains at least a target analyte and a fluorescent labeled probe and wherein a reaction in the sample generates a fluorescent labeled product capable of binding to the capture molecules on the surface of the SPFS sensor; applying a voltage between the first and second reservoirs, wherein an LE-TE interface is formed in the main fluid channel and moves toward the second reservoir; when the LE-TE interface moves to a location of the main fluid channel near the third location, removing the voltage between the first and second reservoirs, and creating a pressure differential between the main fluid channel and the detector chamber to cause the fluid to flow from the main fluid channel via the side channel into the detector chamber; and detecting a fluorescent signal in the detector chamber using the SPFS sensor.

In another aspect, the present invention provides a microfluidic chip for detecting a biological analyte, which includes: a fluid channel; a first reservoir containing a low-mobility trailing electrolyte (TE) buffer and connected to the fluid channel at a first location; a second reservoir containing a high-mobility leading electrolyte (LE) buffer and connected to the fluid channel at a second location, wherein a voltage is applied between the first reservoir and the second reservoir; and a SPFS (surface plasmon field enhanced fluorescence spectroscopy) sensor located at a detection region of the fluid channel, wherein the SPFS sensor has a metal surface which has capture molecules immobilized on it and which forms a part of an inner surface of the fluid channel.

In another aspect, the present invention provides a method for detecting a target analyte, which includes: providing a microfluidic chip having a fluid channel, a first reservoir containing a low-mobility trailing electrolyte (TE) buffer and connected to the fluid channel at a first location, a second reservoir containing a high-mobility leading electrolyte (LE) buffer and connected to the fluid channel at a second location, and a SPFS (surface plasmon field enhanced fluorescence spectroscopy) sensor at a detection region of the fluid channel, wherein the SPFS sensor has a metal surface which has capture molecules immobilized on it and which forms a part of an inner surface of the fluid channel; loading the target analyte and a fluorescent labeled probe into the first reservoir of the microfluidic chip, wherein the target analyte and the fluorescent labeled probe are capable of binding to each other to form a complex, and wherein the complex is capable of binding to the capture molecules on the surface of the SPFS sensor; applying a voltage between the first and second reservoirs; and detecting a fluorescent signal in the detection region.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

It is to be understood that both the foregoing general description and the following detailed description are exemplary and explanatory and are intended to provide further explanation of the invention as claimed.

DETAILED DESCRIPTION OF PREFERRED EMBODIMENTS

A novel combination of SPFS and ITP technologies for detecting biomolecules is disclosed herein. It uses ITP to preconcentrate the reactants and accelerate the reaction, and then delivers the reacted sample to an SPFS sensor for detection. In a particular example, the technique is used in a DNAzyme assay.

Figure 3:
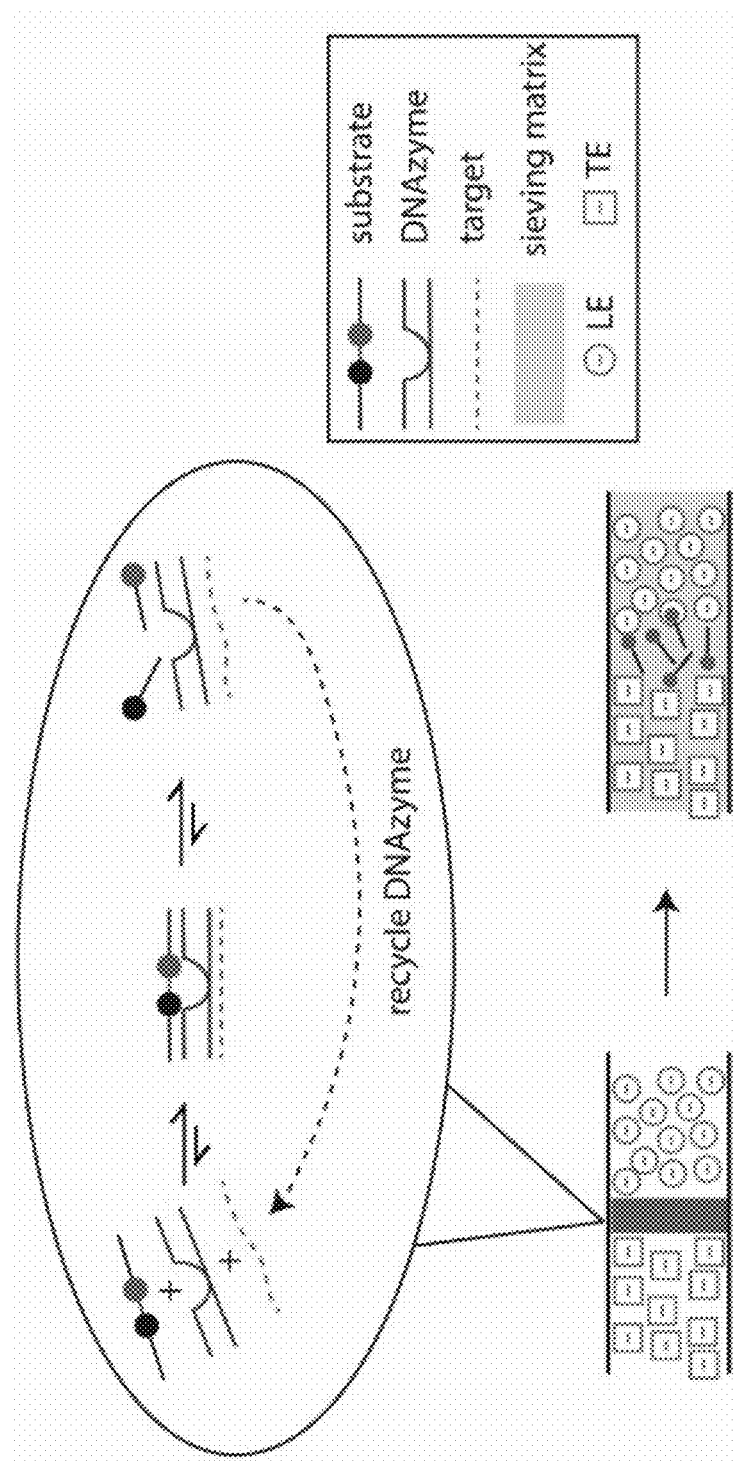
FIG. 3 schematically illustrates the principle of a DNAzyme assay using ITP.

FIG. 3 schematically illustrates the principle of a DNAzyme assay using ITP. In the DNAzyme reaction, the DNAzyme, substrate (also referred to a probe, which is labeled with both a fluorophore and quencher), and target form a complex. As a result, the substrate is cleaved and fluorescent signal increases. The DNAzyme and target are free to react with more substrates. ITP is used to preconcentrate the reaction sample to accelerate nucleic acid hybridization reactions for the DNAzyme. In accordance with embodiments of the present invention, this DNA detection system incorporates an SPFS sensor in the microfluidic device; the cleaved substrate fragment with a fluorescent tag is captured on the SPFS sensor surface for detection.

Due to the high electric field requirements of ITP, it is challenging to integrate ITP with conducting surfaces and/or semiconductor substrates which is required for an SPFS sensor. A first embodiment of the present invention uses a microfluidic device with a T-junction and a two-step technique to integrate ITP with a gold prism SPFS sensor. More specifically, ITP is used to focus and transport target molecules in the vicinity of but not directly over the SPFS sensor. The SPFS sensor is located near the T-junction (within a side channel) of the microfluidic device. A pressure-driven flow is then used to deliver the concentrated sample zone via the side channel to the SPFS sensor. Potential issues of non-specific binding may be solved by introducing a sieving matrix or filter upstream from the T-junction.

The first embodiment of the invention is described in more detail below with reference to FIGS. 4-5.

Figure 4:
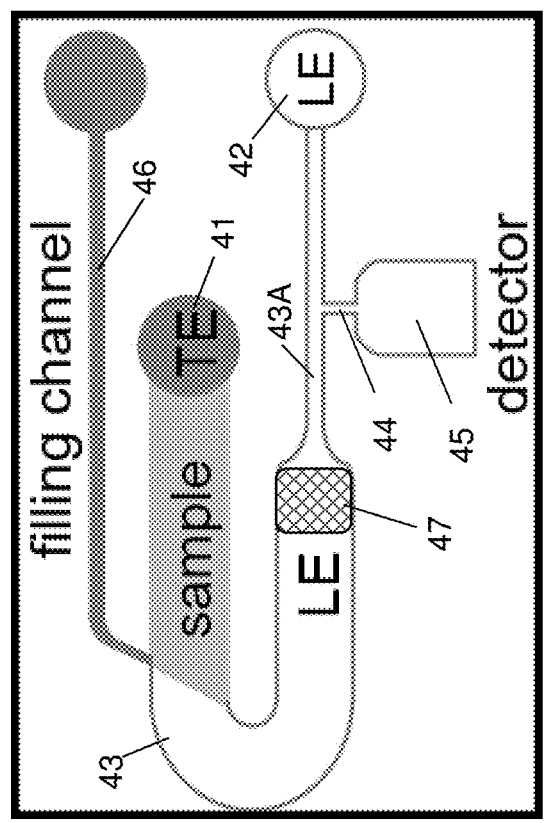
FIGS. 4 and 5 schematically illustrate a microfluidic device for detecting biomolecules using ITP preconcentration combined with SPFS sensing according to a first embodiment of the present invention.

FIG. 4 schematically illustrates a microfluidic device (chip) that combines SPFS and ITP for biomolecule detection according to an embodiment of the present invention.

By using a T-junction, this chip geometry integrates ITP preconcentration followed by pressure-driven delivery of reacted sample to a nearby conductive SPFS sensor region.

Figure 1:
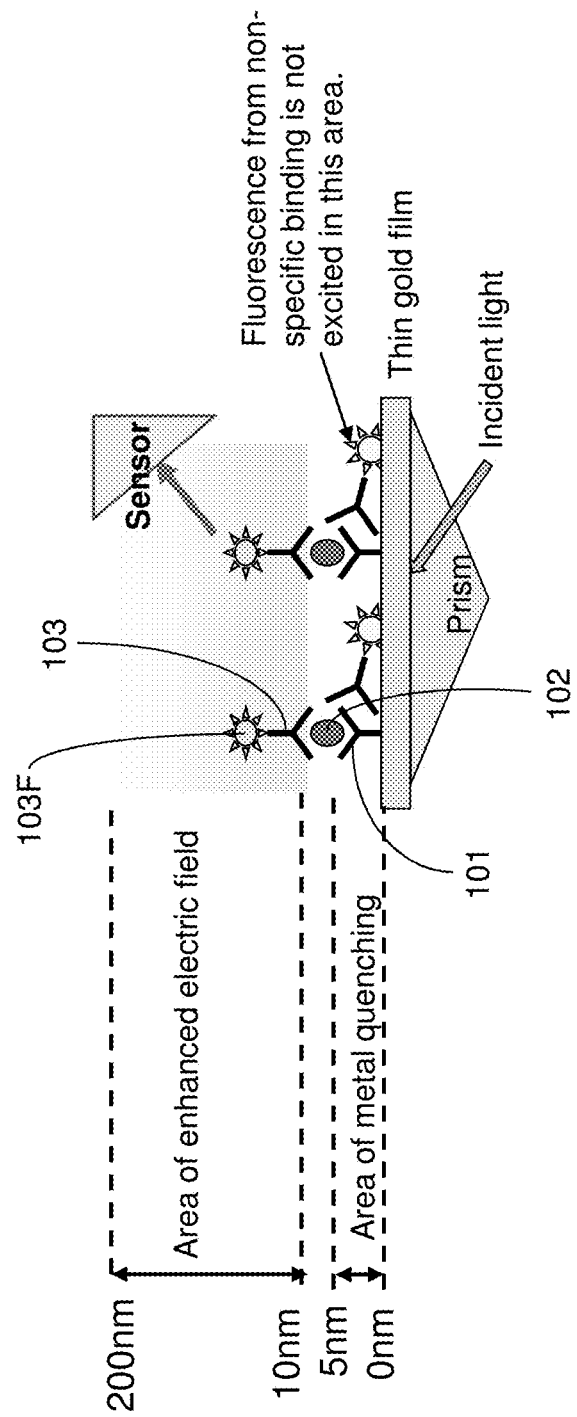
FIGS. 1, 1A and 1B schematically illustrate the principle and setup of a conventional SPFS biosensor.
Figure 1A:
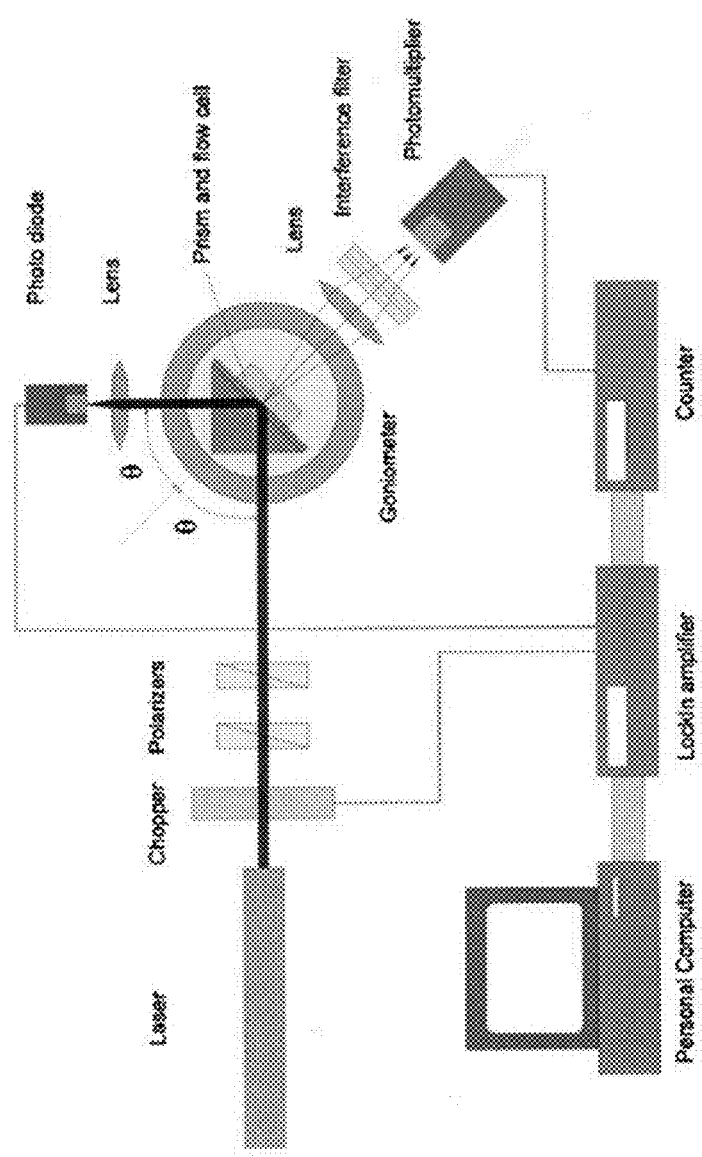
Figure 1B:
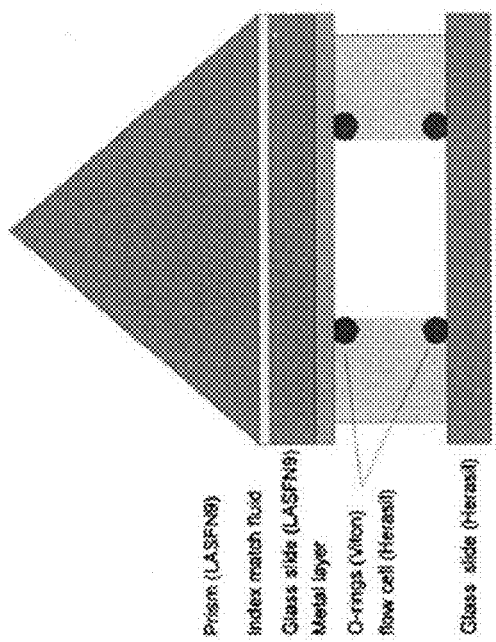
Figure 2:
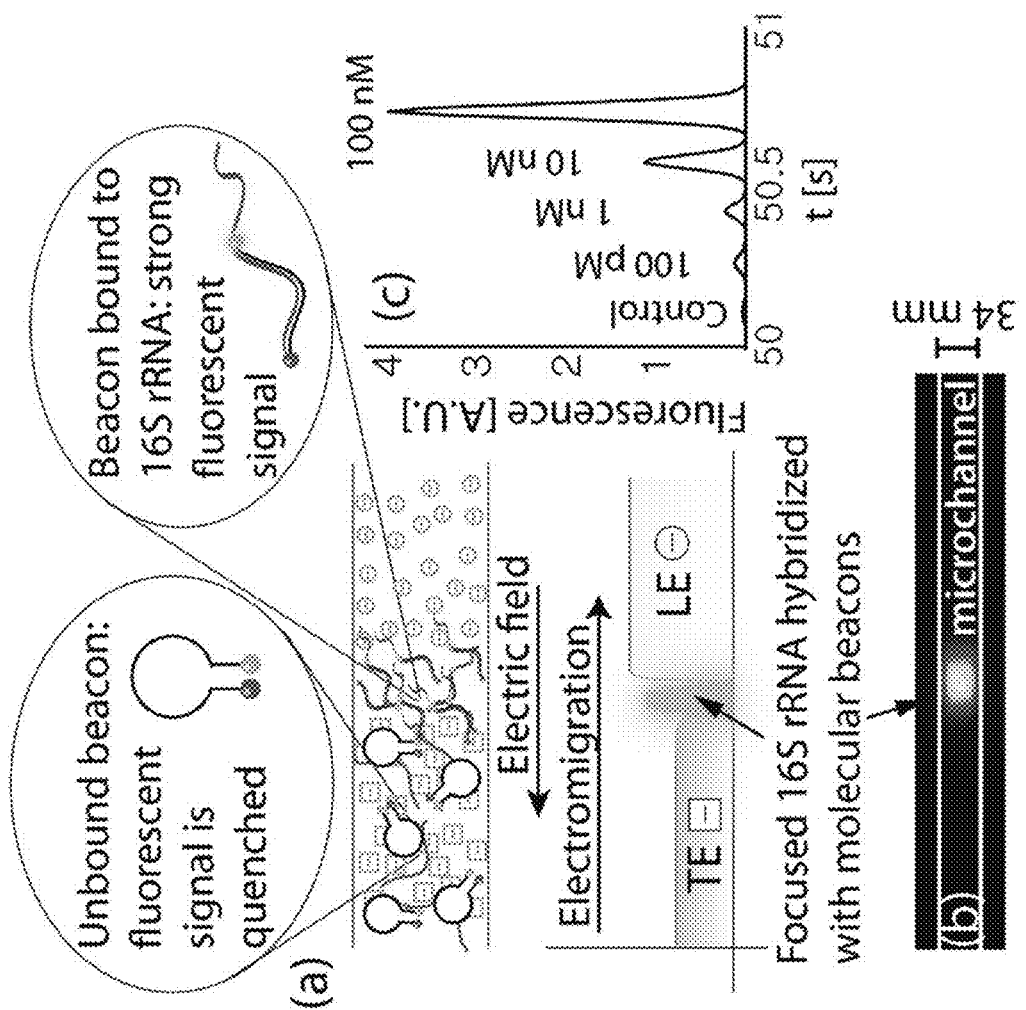
FIGS. 2, 2A and 2B schematically illustrate the principle of a biomolecule detection method using ITP and a setup for the on-chip ITP assay in a known method.
Figure 2A:
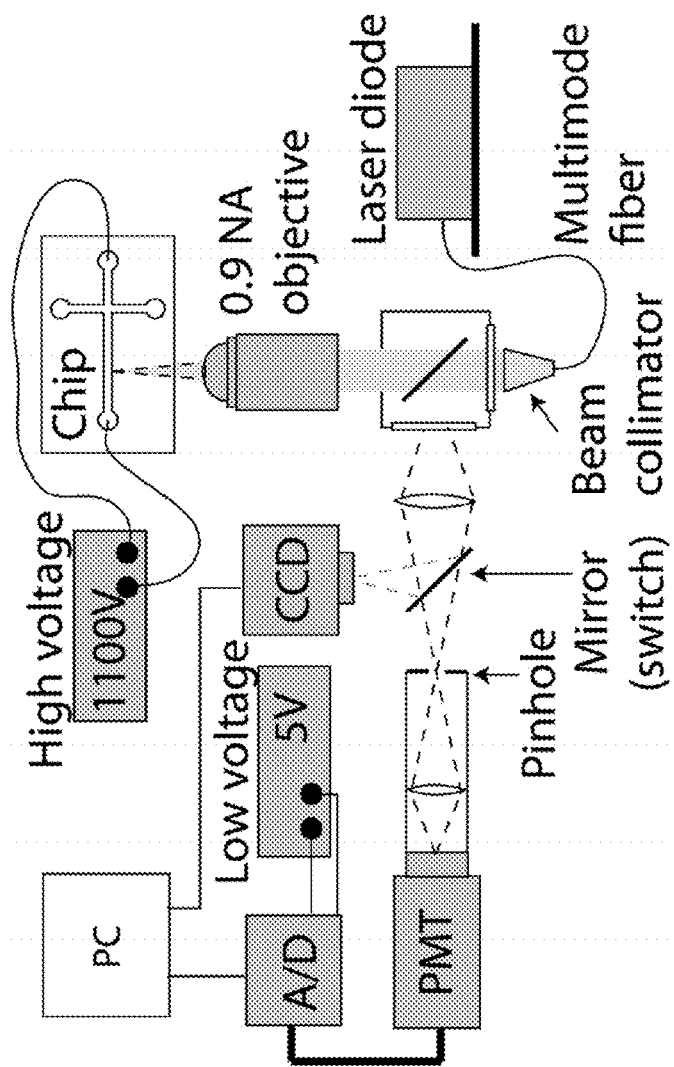
Figure 2B:
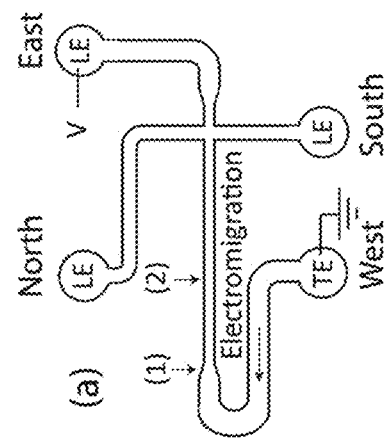

As shown in FIG. 4, the microfluidic device includes a TE reservoir 41, an LE reservoir 42, and a main fluid channel 43 connecting the two reservoirs. A T-junction side channel 44 is joined to the main fluid channel 43 between the two reservoirs, preferably near the LE reservoir 42, and a detector chamber 45 is provided at the other end of the side channel 44 and equipped with an SPFS sensor. The SPFS sensor may have a structure described earlier (see FIGS. 1, 1A and 1B); the SPFS sensor includes a metal surface which has capture molecules immobilized on it and which forms a part of an inner surface of the detector chamber. The capture molecules are capable of capturing the fluorescent labeled component in the reacted sample, e.g. the cleaved substrate fragment with the fluorescent label in the DNAzyme assay. Preferably, a portion 43A of the main channel 43, located at and on both sides of the T-junction where the side channel 44 joins the main channel, has a reduced cross-sectional size to form a constriction section. A filling channel (also referred to as a vacuum port) 46 is connected to the main fluid channel 43 by another T-junction, preferably located near the TE reservoir 41.

Figure 5:
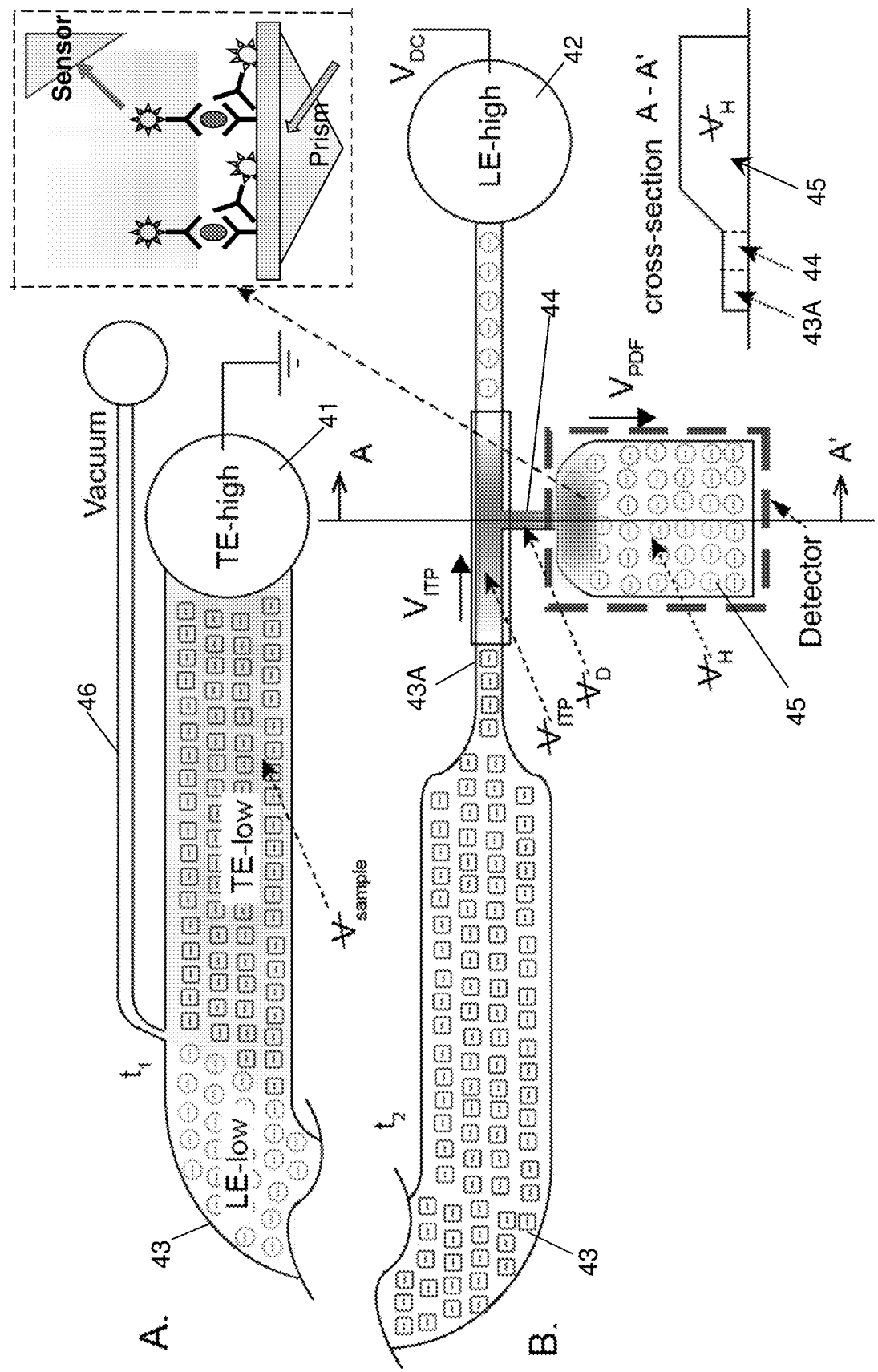

FIG. 5 schematically illustrates the two-step process for detection of biological molecules using the microfluidic device shown in FIG. 4. The process includes step (A), sample loading and ITP extraction and preconcentration, and step (B), delivery of concentrated sample to the detector chamber using pressure-driven flow.

Prior to the assay, the TE and LE reservoirs 41 and 42 are filled with respective electrolyte buffers. Preferably, high ionic strength TE and LE buffers are used in the reservoirs to minimize ion depletion and changes in pH. The detector chamber 45 can be dry before the assay. A biological sample, for example, a sample including a target DNA, a DNAzyme and a fluorescent labeled substrate, is loaded into the TE reservoir 41. The mobility ($\mu$) of the various components in the ITP system should satisfy $\mu_{LE} > \mu_{target}$, $\mu_{DNAzyme}$, $\mu_{substrate} > \mu_{TE}$. Note that in this disclosure, the term "mobility" refers to the magnitude of or absolute value of the electrophoretic mobility of the electrolyte ion.

Then, a vacuum is applied via the vacuum port 46, causing the two liquid volumes (the volume containing TE and the volume containing LE with sample) to merge together and form a sharp interface. Preferably, the height (i.e. the dimension in the direction perpendicular to the drawing sheet) of the vacuum port 46 is smaller than the height of the main channel 43, which allows for sample loading with minimal sample loss.

A voltage is then applied to the TE and LE reservoirs to generate an electric field to initiate ITP. In the ITP process (referred to here as ITP preconcentration), the reactants in the sample are extracted and accumulated (focused) by ITP at the LE-TE interface. As a result, the biological reaction (DNA hybridization reaction in this example) is significantly accelerated.

During the ITP preconcentration process, the detector chamber 45 remains dry so as to prevent leakage of sample ions into the chamber. When the ITP preconcentration is completed and the LE-TE interface reaches the constriction section 43A of the fluid channel, the voltage applied to the TE and LE reservoirs is turned off. The pressure between the main fluid channel 43 and the detector chamber 45 is then controlled so as to cause concentrated sample to flow from the region 43A into the detector chamber 45. One method of doing this is to apply positive pressure to channel 46.

Alternately, a second method is to apply pressure simultaneously to the reservoirs 41 and 42 and the reservoir of channel 46. The flow caused by this channel-to-detector-chamber pressure differences is here referred to as pressure-driven flow.

In a preferred embodiment, the detector chamber 45 is a closed, dead-end delivery chamber. The pressure difference between section 43a and the detector chamber 45 forces the air-liquid meniscus into the chamber 45. One or more walls of the chamber are constructed from a substrate such as polydimethylsiloxane (PDMS) which is permeable to gas, enabling dead-end filling (i.e. air exits through the PDMS). Preferably, the volume ratio of the side channel 44 and the detector chamber 45 is small, and this enables delivery to the chamber of only liquid near the LE-TE interface, i.e. liquid containing preconcentrated sample species.

In an alternatively embodiment, in lieu of a positive pressure applied through the vacuum channel 46 (or simultaneously to the reservoirs 41 and 42 and the reservoir of channel 46), a negative pressure (vacuum) is applied to the detector chamber 45 to cause the sample to flow into the detector chamber from the main fluid channel 43. In this alternative embodiment, the detector chamber 45 may not be closed chamber, but has a port through which vacuum can be applied. Both methods may be used to create a pressure differential between the main fluid channel and the detector chamber to cause the pressure-driven flow of the sample from the main fluid channel into the detector chamber.

In yet another embodiment, a vacuum is applied to the PDMS region immediately adjoining detector chamber 45 and this causes air to flow through the PDMS and for liquid to enter and eventually fill the detector chamber 45 from region 43A.

In the detector chamber 45, the cleaved fragment of the substrate that contains the fluorescent label is captured by capture molecules immobilized on the sensor surface, and is detected using the SPFS mechanism described earlier, i.e. by irradiating an incident light on the SPFS sensor and detecting the output fluorescent signal.

As shown in FIG. 5, the height of the detector chamber 45 is preferably larger than the height of the constriction section 43A and the height of the side channel 44. Preferably, the volume of the side channel 44, denoted $V_D$, is smaller than the volume of the portion of the constriction where the preconcentrated sample is present, denoted $V_{ITP}$. Further, the volume $V_D$ of the side channel 44 is preferably less than about 20% of the volume of the detector chamber 45, denoted $V_H$. One purpose of such volume constraints of the microfluidic device is to minimize sample dispersion when delivering the ITP-focused sample to the SPFS detector.

The design of the microfluidic device described above may be referred to as a 3D-chip in that the chip may have different heights in different sections. In a preferred embodiment, the chip is capable of achieving efficient ITP preconcentration of target from small volume samples (such as 1000µl). The design takes into consideration ITP separation capacity, extraction efficiency, pH buffering capacity, and minimization of sample dispersion by diffusion.

By designing the TE buffer so that the DNAzyme, substrate, and target all focus in ITP, the assay can be significantly sped up, and assay time can be significantly reduced, for example, from a few hours (without using ITP) to 10 min.

Referring back to FIG. 4, a sieving matrix 47 may be optionally provided in the main fluid channel 43, upstream from the T-junction of the side channel 44, to separate cleaved from uncleaved substrate when greater dynamic range is desired. This reduces the amount of uncleaved substrate with fluorescent labels in the sample delivered to the detector chamber 45. Alternatively, a filter that binds the uncleaved substrate may be employed in lieu of the sieving matrix 47. Additionally, the voltage applied to the LE and TE reservoirs may be controlled to reduce the velocity of the LE-TE interface as it passes through the filter to allow more effective capture of the uncleaved substrate.

Although DNAzyme is used as a specific example in the above descriptions, the above-described microfluidic device and detection method can be used to detect various analytes such as nucleic acids, proteins, metabolites, viruses, bacteria, cells, antibodies, etc.

Figure 6:
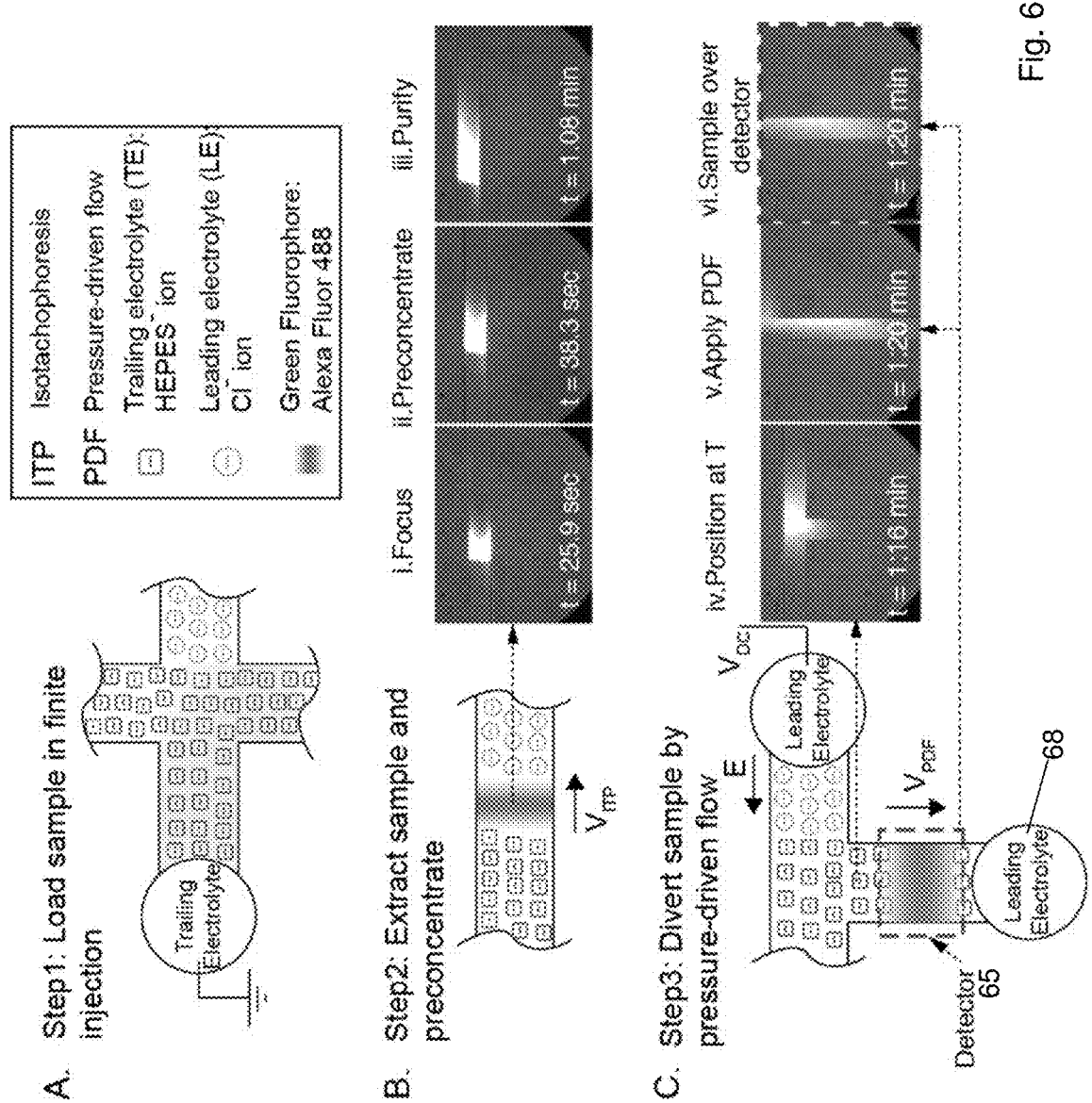
FIG. 6 schematically illustrates a microfluidic device for detecting biomolecules using ITP preconcentration combined with SPFS sensing according to an alternative embodiment of the present invention.

FIG. 6 schematically illustrates a microfluidic device that combines a designated detection region and ITP for biomolecule detection according to an alternative embodiment of the present invention. The microfluidic device is generally similar to that shown in FIGS. 4 and 5, but the detector chamber 65 is a region in the side channel between the t-junction and another LE reservoir 68 downstream of the detector chamber. As shown in panel (A), a low concentration sample is loaded in the reservoir with trailing electrolyte and introduced to the injection channel by a vacuum. In panel (B), sample is extracted and accumulated in the ITP interface. The figure insets show epifluorescence images of fluorescent sample focusing, preconcentration, and purification from inhibitors and contaminants. In panel (C), the accumulated sample is diverted by pressure flow to the side channel overlaying the detector 65. The figure insets show typical experimental images of an ITP zone migrating, and sample positioning near the T-junction. After voltage is turned off (just after image iv), the ITP zone is introduced into the side channel via pressure-driven flow (PDF). The concentrated sample is subsequently positioned into a detection region within the side channel (in this experiment, detected only using fluorescence).

FIGS. 7-12 illustrate a biomolecule detection method combining SPFS and ITP according to a second embodiment of the present invention and its variations. In the second embodiment, the SPFS detector is located on the main fluid channel between the LE and TE reservoirs.

In the second embodiment and its variations, the potential challenges caused by the SPFS and ITP combination, such as short reaction time and non-specific binding, can be overcome by using various techniques described below. To summarize, the potential problem of short reaction time is solved by extending the concentrated sample retention time on the SPFS sensor surface, specifically, (1) by controlling sample movement speed by voltage control (slow down, stop, reverse, etc.), and/or (2) by expanding the capture area of the SPFS sensor. The non-specific binding is reduced by (1) introducing a filter upstream from the SPFS sensor, and/or (2) using a special wash buffer.

Figure 7:
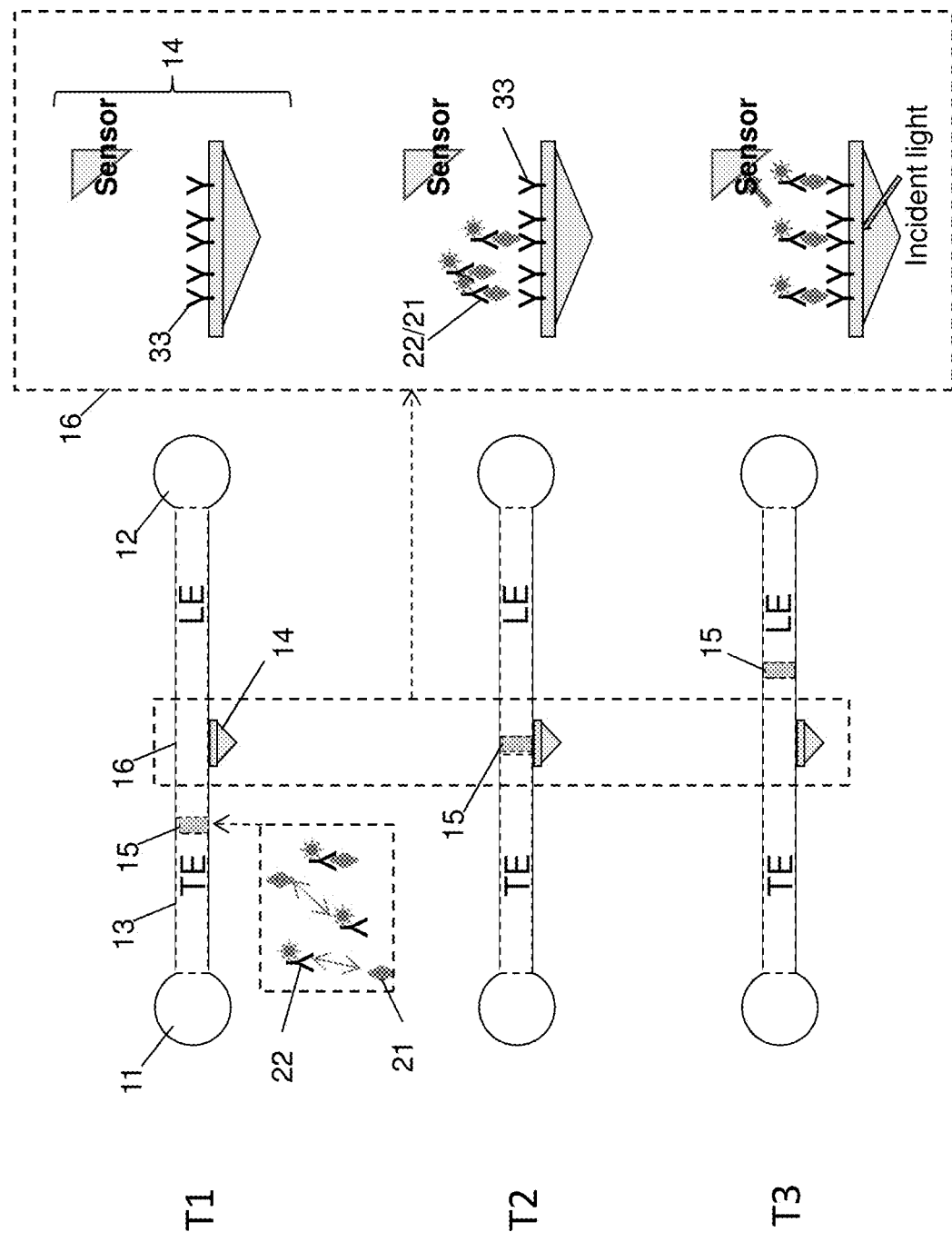
FIG. 7 schematically illustrates the principle of a biomolecule detection method combining SPFS and ITP according to a second embodiment of the present invention.

FIG. 7 schematically illustrates the principles of a method that combines SPFS and ITP according to an embodiment of the present invention. An ITP setup, including a TE reservoir 11, an LE reservoir 12, and a fluid channel 13 connecting the two, is equipped on the SPFS sensor 14, such that the solution in the fluid channel passes and contacts the SPFS sensor surface (i.e. the surface of the thin metal film on the prism) between the TE reservoir and the LE reservoir. In time period T1, target analytes 21 and fluorescent labeled probes 22 which have been loaded into the TE reservoir 11 are focused 15 in a region of the fluid channel upstream from the SPFS sensor region 16, and they are reacted (i.e. the target analyte binds to the probes). In time period T2, the focused sample 15 travels downstream to reach the SPFS sensor region 16, and the analyte-probe complexes are captured by capture molecules 33 immobilized on the sensor surface. In time period T3, after the focused sample 15 completely passes through the SPFS sensor region 16, captured fluorescent molecules 21/22 on the sensor surface 16 are detected using the SPFS mechanism, i.e. by irradiating an incident light on the SPFS sensor and detecting the output fluorescent signal. The mobility ($\mu$) of the various components in the ITP system should satisfy $\mu_{LE} > \mu_{target}$, $\mu_{labeled\ probe} > \mu_{TE}$.

Figure 8:
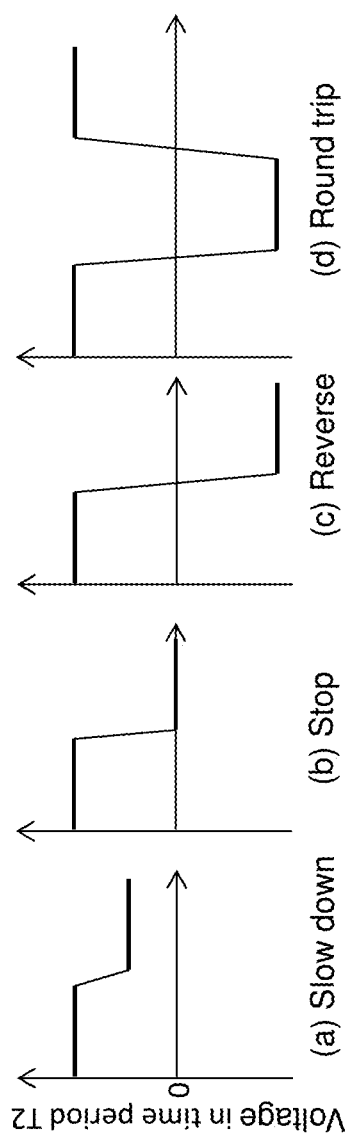
FIGS. 8, 9(a) and 9(b) schematically illustrate two methods for extending the concentrated sample retention time according to variations of the embodiment.
Figure 9A:
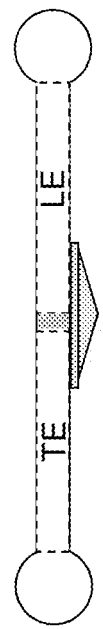
Figure 9B:
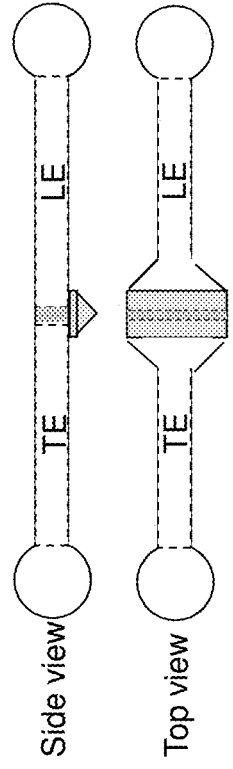

FIGS. 8, 9(a) and 9(b) schematically illustrate two methods for extending the concentrated sample retention time, i.e. the time duration that the concentrated sample is located within the region 16 of the microchannel above the SPFS sensor surface.

The first method involves changing the voltage applied between the TE and LE reservoirs 11 and 12 in the ITP setup. As shown in FIG. 8, in time period T2, i.e. when the focused sample reaches the SPFS sensor region 16, voltage profile (a) which applies a reduced voltage level may be used to slow down the sample in the sensor region; voltage profile (b) where the voltage is reduced to zero may be used to stop the sample in the sensor region; voltage profile (c) which applies a voltage of a reversed polarity may be used to cause the sample to travel in the reverse direction in the sensor region; and voltage profile (d) which applies voltages of alternating polarities may be used to cause the sample to repeatedly travel back and forth in the sensor region. Combinations of the above voltage profiles can also be used. The voltage can be changed either in a gradual manner or in a discrete manner. A DC voltage is used in the above examples, but an AC voltage can be also used.

It should be noted that a lower voltage or a zero voltage causes the focused sample band to be diffused, which is not desirable; therefore, in determining the voltage control pattern, there is a tradeoff between extending the sample retention time and maintaining concentration of the sample.

The timing of when the concentrated sample will reach the sensor region can be calculated using expected sample migration speed ($V_{ITP} = \mu_{LE} * E_{LE}$) in advance, and voltage variation control can be started at that time. Alternatively, the timing of when the concentrated sample reaches the sensor region can be detected by detecting the fluorescent molecules in the sample using the SPFS sensor during the test. As another alternative, a colored material which has a mobility $\mu_{color}$ satisfying ($\mu_{LE} > \mu_{color} \geq \mu_{target}, \mu_{labeled\ probe}$) is mixed with the sample and used for position monitoring.

The second method for extending the concentrated sample retention time involves increasing the size of the SPFS sensor surface, as shown in FIGS. 9(a) and 9(b). The SPFS sensor surface can be increased in the direction parallel to the travel direction of the sample solution (i.e. along the fluid channel) (FIG. 9(a)), or in the direction perpendicular to the travel direction (FIG. 9(b)), e.g. by aligning multiple capillaries. It is preferable that the width (i.e. the dimension in the sample travel direction) of the sensor surface area is larger than the width of sample band focused by ITP, so as to increase the time that the sample is located in the sensor region. It should be noted that if the sensor surface area is increased, the irradiation light and the prism of the SPFS device also need to be increased to detect the signals from the entire sensor surface area.

Figure 10:
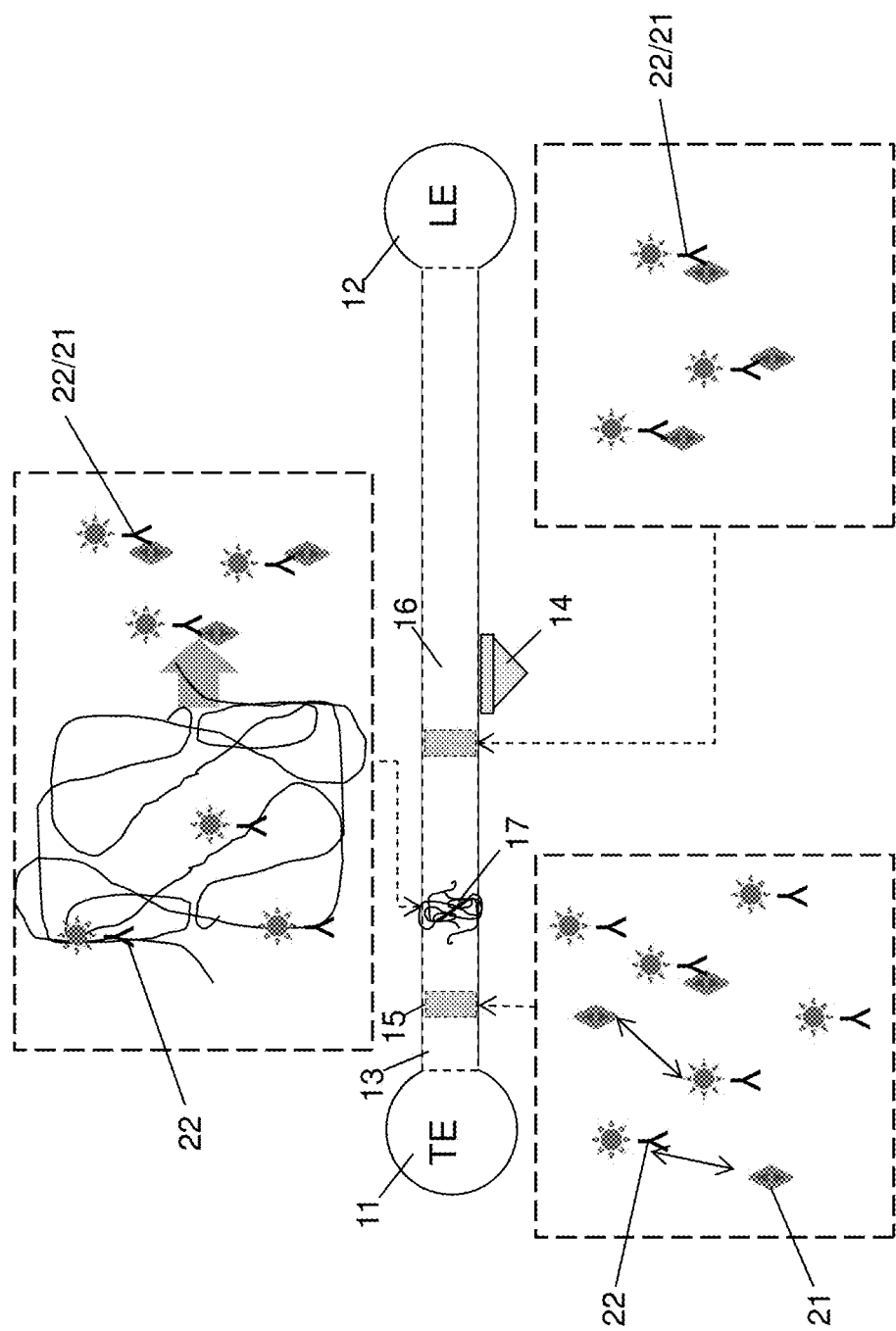
FIG. 10 schematically illustrates a method and setup for reducing non-specific binding in the biomolecule detection method according to another variation of the second embodiment.

A method for reducing non-specific binding is illustrated in FIG. 10. A filter 17, located in the fluid channel 13 between the TE reservoir 11 and the SPFS sensor region 16, is used to capture unbound labeled probes 22, whereas the probe-analyte complex 22/21 passes through the filter. When the concentrated sample reaches the filter 17, the applied voltage is controlled (e.g., similar to the examples shown in FIG. 8) to cause the sample to slow down, stop, reverse, or travel back and forth, in order to increase the capture of the unbound labeled probe by the filter. It should be noted that the location of the filter 17 should allow the binding of the probe 22 and the analyte 21 to occur sufficiently before the sample reaches the filter.

Another method (not shown in the drawings) for reducing non-specific binding is to use a TE buffer that has a strong wash effect to wash off the non-specifically bound fluorescent molecules (labeled probed) from the SPFS sensor surface. Generally speaking, the requirements for the TE buffer are not very strict and it is not difficult to find appropriate wash buffers that will be suitable as the TE buffer. Examples of strong wash buffers that can be used as the TE buffer include surfactants such as TritonX-100, Tween 20, etc.

Figure 11:
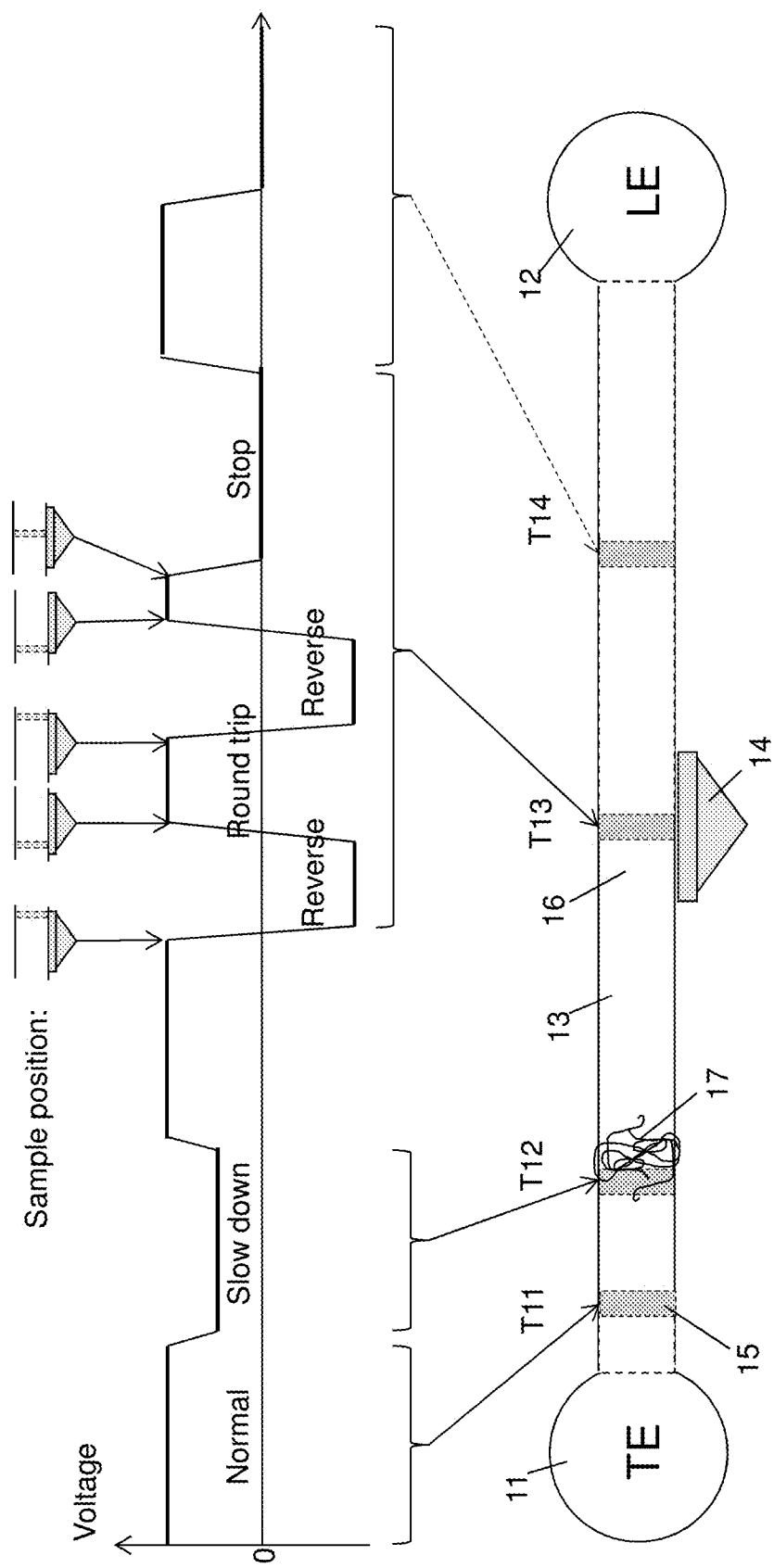
FIG. 11 illustrates an example of a voltage control sequence in a detection method using ITP equipped with a filter and SPFS sensor according to another variation of the second embodiment.

FIG. 11 illustrates an example of a voltage control sequence in a detection method using ITP equipped with a filter 17 and SPFS sensor 14 according to an embodiment of the present embodiment. During time period T11, when the sample band is located between the TE reservoir 11 and the filter 17, a normal voltage is applied to focus the sample 15. During time period T12, when the sample band is in the filter or its vicinity, the voltage is decreased and the sample moving speed is slowed down. During time period T13, the voltage is changed multiple times when the sample band is located within the sensor region 16. Within this time period, when the sample band first reaches the downstream edge of the SPFS sensor region 16 closer to the LE reservoir 12 (i.e. after the sample band has substantially passed through the sensor region), the voltage polarity is reversed and the sample moving direction is reversed. Then, when the sample reaches the upstream edge of the sensor region close to the TE reservoir (i.e. after the sample has substantially moved backward past the sensor region), the voltage is changed again to the original (normal) polarity. These "round trip" voltage changes can be done multiple times to cause the sample to make round trip movements in the sensor region. After the round trip movement, the sample is stopped in the center of the sensor region for a desired amount of time. During time period T14, the normal voltage is applied and the sample leaves the sensor region and moves towards the LE reservoir. At some time during this period (any time after the sample has left the sensor region), SPFS detection is conducted. During detection, the voltage can be turned off. As an alternative, a reverse voltage can be applied during the time period T14, to make the sample migrate towards the TE reservoir, as long as the sample is not in the sensor surface region when SPFS detection is conducted.

Using the above-described method, various analytes can be detected, including nucleic acids, proteins, metabolites, viruses, bacteria, cells, antibodies, etc. The mobility ($\mu$) of the various components should satisfy $\mu_{LE} > \mu_{target}$, $\mu_{labeled\ probe} > \mu_{TE}$.

Further, DNAzyme amplification and separation mechanisms described in commonly-owned U.S. patent application Ser. No. 14/590,482, publication No. US 2015/0197791 (which is incorporated by reference herein) can be used in combination with SPFS techniques (see FIG. 12). US 2015/0197791 describes a "DNA detection method [which] combines DNAzyme reactions and on-chip isotachophoresis (ITP). A mixture of sample containing a target DNA and a DNAzyme sensor which is either (1) a catalytic molecular beacon or (2) a binary DNAzyme and a probe is loaded into a trailing electrolyte (TE) reservoir of a microfluidic chip. In the presence of the target DNA, the catalytic molecular beacon or the probe is cleaved to generate a fluorescent fragment. Enhanced DNAzyme reaction occurs at the TE-to-LE interface. Fluorescent signal from cleaved catalytic molecular beacon or probe is detected either at the location where DNAzyme reaction occurs or at a separate location. In the latter case, the microfluidic chip has a separation region containing a capture gel or a sieving matrix which allows the fluorescent fragment to pass through but captures or traps the uncleaved catalytic molecular beacon or probe." (Id., Abstract.) This DNA detection method can be modified by incorporating an SPFS sensor in the microfluidic system in the manner shown in FIG. 12, so that the cleaved fragment which has a fluorescent tag can be captured on the SPFS sensor surface for detection.

Figure 12:
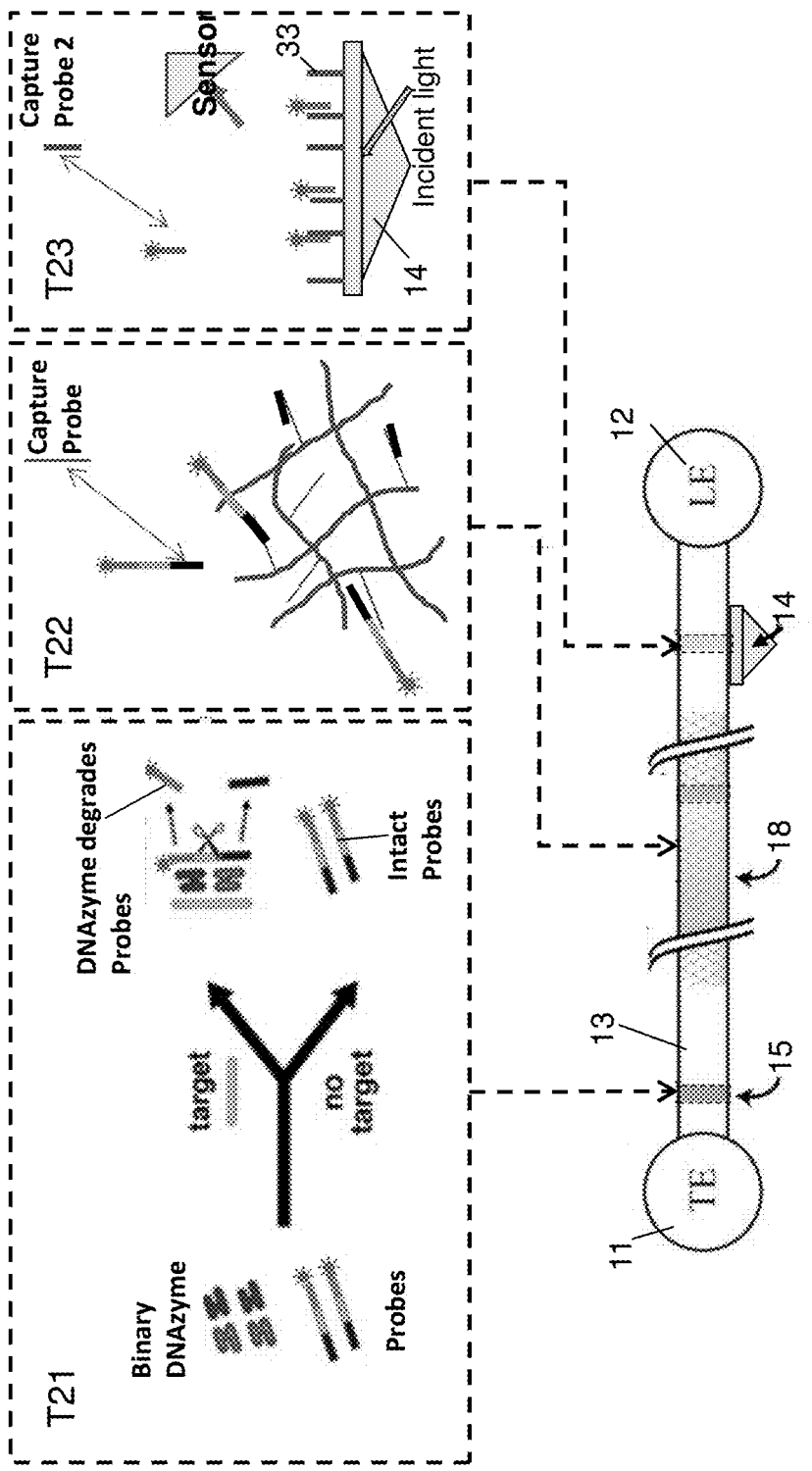
FIG. 12 schematically illustrates a DNA detection method employing DNAzyme amplification and separation mechanisms in combination with ITP and SPFS techniques according to another variation of the second embodiment.

More specifically, as shown in FIG. 12, during time period T21, DNAzyme reaction (enhanced hybridization) occurs in the focused sample 15 in a region (referred to as the DNAzyme reaction region) of the fluid channel 13 between the TE 11 and a capturing region 18. During time period T22, the sample 15 moves through the capturing region 18 where intact probes are captured by a matrix which has a capture probe immobilized on it. During time period T23, the sample 15 moves to the detection region above the surface of the SPFS sensor 14, where the degraded probes are detected.

Various modifications and improvements may be made to the above-described systems. As described in the Han et al. Lab on a Chip 2014 article "Increasing hybridization rate and sensitivity of DNA microarrays using isotachophoresis," a narrow constriction can be equipped in the region upstream of the SPFS sensor, in order to make homogenous sample solution.

It is preferable to increase the sample volume to obtain higher signals. In the current ITP configuration, limitation of sample volume can be one of the challenges. One of the solutions can be to use a large sample reservoir.

The ITP chip shape is not necessarily straight. In order to avoid possible short circuit problem caused by SPFS gold sensor chip, other shape such as U-shape can be used. In another embodiment to avoid possible shot circuit problem, stripe gold sensor chip which has about a couple of ten micro meter pitch gold layer can be used.

One advantage of the microfluidic device that combines ITP and SPFS is that, because the fluorescent labeled probes are captured by the SPFS sensor surface, there is flexibility in the timing of signal detection, that is, there is no need to detect the signal at a fixed timing.

The content of the parent application, U.S. patent application Ser. No. 14/995,112, filed Jan. 13, 2016, is herein incorporated by reference in its entirety.

It will be apparent to those skilled in the art that various modification and variations can be made in the detection method of the present invention without departing from the spirit or scope of the invention. Thus, it is intended that the present invention cover modifications and variations that come within the scope of the appended claims and their equivalents.

What is claimed is:

1. A microfluidic chip for detecting a biological analyte, comprising:
   a main fluid channel;
   a first reservoir containing a low-mobility trailing electrolyte (TE) buffer and connected to the main fluid channel at a first location;
   a second reservoir containing a high-mobility leading electrolyte (LE) buffer and connected to the main fluid channel at a second location;
   a side fluid channel connected at its first end to the main fluid channel at a third location between the first reservoir and the second reservoir; and
   a detector chamber connected to a second end of the side channel, the detector chamber being equipped with a sensor, wherein the sensor has an electrically conductive surface which has capture molecules immobilized on it and which forms a part of an inner surface of the detector chamber,
   wherein the detector chamber is a closed, dead-end delivery chamber, and wherein one or more walls of the detector chamber are constructed from a substrate which is permeable to gas.

2. The microfluidic chip of claim 1, wherein the sensor is an SPFS (surface plasmon field enhanced fluorescence spectroscopy) sensor.

3. The microfluidic chip of claim 1, wherein the third location is near the second reservoir.

4. The microfluidic chip of claim 1, wherein a section of the main fluid channel located at and on both sides of the third location has a reduced cross-sectional size to form a constriction section.

5. The microfluidic chip of claim 4, wherein a height of the detector chamber is larger than a height of the constriction section of the main fluid chamber and a height of the side fluid channel.

6. The microfluidic chip of claim 1, wherein a volume of the side fluid channel is less than 20% of a volume of the detector chamber.

7. A microfluidic chip for detecting a biological analyte, comprising:
   a main fluid channel;
   a first reservoir containing a low-mobility trailing electrolyte (TE) buffer and connected to the main fluid channel at a first location;
   a second reservoir containing a high-mobility leading electrolyte (LE) buffer and connected to the main fluid channel at a second location;
   a side fluid channel connected at its first end to the main fluid channel at a third location between the first reservoir and the second reservoir;
   a detector chamber connected to the side channel, the detector chamber being equipped with a sensor, wherein the sensor has an electrically conductive surface which has capture molecules immobilized on it and which forms a part of an inner surface of the detector chamber, wherein the detector chamber includes a port; and
   a vacuum source coupled to the port of the detector chamber for applying a vacuum to the detector chamber.

8. The microfluidic chip of claim 7, wherein the sensor is an SPFS (surface plasmon field enhanced fluorescence spectroscopy) sensor.

9. The microfluidic chip of claim 7, wherein the third location is near the second reservoir.

10. The microfluidic chip of claim 7, wherein a section of the main fluid channel located at and on both sides of the third location has a reduced cross-sectional size to form a constriction section.

11. The microfluidic chip of claim 10, wherein a height of the detector chamber is larger than a height of the constriction section of the main fluid chamber and a height of the side fluid channel.

12. The microfluidic chip of claim 7, wherein a volume of the side fluid channel is less than 20% of a volume of the detector chamber.

\* \* \* \* \*